(12) United States Patent
Rash

(10) Patent No.: US 11,364,025 B2
(45) Date of Patent: Jun. 21, 2022

(54) SUTURE PASSER

(71) Applicant: Elad Rash, Beit Lehem Glilit (IL)

(72) Inventor: Elad Rash, Beit Lehem Glilit (IL)

( * ) Notice: Subject to any disclaimer, the term of this patent is extended or adjusted under 35 U.S.C. 154(b) by 307 days.

(21) Appl. No.: 16/480,324

(22) PCT Filed: Jan. 24, 2018

(86) PCT No.: PCT/IL2018/050087
§ 371 (c)(1),
(2) Date: Jul. 24, 2019

(87) PCT Pub. No.: WO2018/138722
PCT Pub. Date: Aug. 2, 2018

(65) Prior Publication Data
US 2021/0275165 A1 Sep. 9, 2021

Related U.S. Application Data

(60) Provisional application No. 62/449,622, filed on Jan. 24, 2017.

(51) Int. Cl.
*A61B 17/04* (2006.01)

(52) U.S. Cl.
CPC ................ *A61B 17/0469* (2013.01)

(58) Field of Classification Search
CPC ............ A61B 17/0469; A61B 17/0491; A61B 17/0482
See application file for complete search history.

(56) References Cited

U.S. PATENT DOCUMENTS

| 2002/0111534 A1 | 8/2002 | Pasricha |
| 2002/0138084 A1* | 9/2002 | Weber ................ A61B 17/0469 606/139 |
| 2010/0113873 A1* | 5/2010 | Suzuki ............... A61B 1/00183 600/106 |

FOREIGN PATENT DOCUMENTS

| EP | 1243221 | 9/2002 |
| WO | 9625885 | 8/1996 |

* cited by examiner

*Primary Examiner* — Kelly J Bekker
*Assistant Examiner* — Mohammed S Adam
(74) *Attorney, Agent, or Firm* — JMB Davis Ben-David

(57) ABSTRACT

A suture passer is provided, defining a longitudinal axis and comprising a jaw assembly configured to be operated to selectively grip an internal tissue of a patient, and a needle mechanism configured to be operated to place a suture on the tissue. The assembly comprises a stationary first jaw portion and a second jaw portion pivotable about a jaw axis with respect to the first jaw portion between a closed position and an open position, the jaw assembly being configured to hold a thread for the suture. The needle mechanism comprises a needle being configured for piercing the tissue and pulling the thread from the jaw assembly, and a carrying member at a first end thereof being pivotable, independently of the second jaw portion, with respect to the first jaw portion, the needle being hingedly articulated to a second end of the carrying member.

19 Claims, 10 Drawing Sheets

SUTURE PASSER

CROSS-REFERENCE TO RELATED APPLICATIONS

This is the U.S. National Stage of International Patent Application No. PCT/IL2018/050087 filed Jan. 24, 2018, which claims priority to U.S. Provisional Patent Application No. 62/449,622 filed Jan. 24, 2017.

TECHNOLOGICAL FIELD

The presently disclosed subject matter is directed toward medical devices for facilitating suture placement. In particular, it is directed toward suture passers for placement of sutures on internal tissue during a minimally invasive surgical procedure.

BACKGROUND

Procedures for repairing internal tissues, for example reattaching tendons, ligaments, bones, etc., are increasingly being performed in a minimally invasive manner. In such procedures, incisions are formed in a patient's skin in the vicinity of the injury, and instruments are inserted subcutaneously in order to repair the tissue. Often, one or more camera and/or other suitable scopes are inserted as will in order to facilitate observation of the procedure.

Suture passers are commonly employed to place a suture on one or more tissues during a minimally invasive procedure. Typically, they include a longitudinal cannula carrying an assembly for gripping the tissue, and a needle for pulling a thread therethrough to form the suture.

SUMMARY

According to one aspect of the presently disclosed subject matter, there is provided a suture passer defining a longitudinal axis and comprising a jaw assembly configured to be operated to selectively grip an internal tissue of a patient, and a needle mechanism configured to be operated to place a suture on the tissue; the jaw assembly comprising a stationary first jaw portion and a second jaw portion pivotable about a jaw axis with respect to the first jaw portion between a closed position and an open position, the jaw assembly being configured to hold a thread for the suture; the needle mechanism comprising a needle being configured for piercing the tissue and pulling the thread from the jaw assembly, and a carrying member pivotable at a first end thereof with respect to the first jaw portion; wherein the carrying member is pivotable independently of the second jaw portion at least when the second jaw portion is in its closed position; wherein the jaw assembly further comprises a pivoting arrangement configured to facilitate hingedly articulating the first and second jaw portions, the pivoting arrangement being free of a member traversing the jaw assembly parallel to the jaw axis; wherein the needle is hingedly articulated to a second end of the carrying member between an extended position in which it is disposed distally to the carrying member along a longitudinal axis thereof, an open position in which it is disposed substantially perpendicular to the carrying member, and a closed position in which it lies in registration therewith; wherein the needle mechanism further comprises a biasing member configured to urge the needle from its closed position into its open position, and a positioning element configured to urge the needle from its extended position to its open position, the biasing member and positioning element being configured to maintain the needle in its open position; and wherein the needle mechanism further comprises a locking arrangement configured to selectively impede pivoting of the needle when in its open position.

The suture passer may further comprise a closing arrangement configured to bring the needle to its closed position when the carrying member is pivoted toward the jaw assembly. The jaw assembly may constitute a portion of the closing arrangement.

One of the jaw portions may be formed, on a surface facing the other jaw portion, with a transverse groove for holding the thread. The jaw portion formed with the groove and the needle assembly may be disposed on opposite sides of the other jaw portion (i.e., the other jaw portion may be disposed between, on one side, the jaw portion formed with the groove and, on the other side, the needle assembly.) A surface of the other jaw portion facing the needle assembly is formed with a seat configured to at least partially receive therein the needle assembly.

The first jaw portion may be formed with the groove.

The first and second jaw portions may each be formed with a longitudinal slot, configured to allow passage therethrough of the needle in its open position.

The pivoting arrangement may comprise axially spaced hinge members and corresponding sockets for receiving and permitting rotation therein of the hinge members. The hinge members may project from a proximal end of the second jaw portion.

The suture passer may further comprise a jaw actuator configured to control pivoting of the second jaw portion, and a carrier actuator configured to control pivoting of the carrier portion, independently of the jaw actuator. The suture passer may further comprise a handle mechanism configured to facilitate a user to selectively and independently operate the jaw and carrier actuators. The handle mechanism may be configured such that operation of the carrier actuator to pivot the carrying member to a closed position also operates the jaw actuator to pivot the second jaw portion to its closed position.

The positioning element may comprise a flat spring.

The locking arrangement may comprise facing cooperating surfaces of the needle and carrying members, the surfaces being configured to be selectively engaged with each other to impede the pivoting of the needle. The cooperating surfaces may be planar. The cooperating surfaces may be formed with non-planar surfaces. One of the cooperating surfaces may comprise a projection, with the other of the cooperating surfaces comprising a corresponding aperture configured to receive it when the needle is in its open position.

The needle may comprise an oblong aperture receiving a pin therewithin, configured to facilitate the needle to be displaced longitudinally, when in its open position, toward the carrying member, thereby engaging the cooperating surfaces.

According to another aspect of the presently disclosed subject matter, there is provided a suture passer defining a longitudinal axis and comprising a jaw assembly configured to be operated to selectively grip an internal tissue of a patient, and a needle mechanism configured to be operated to place a suture on the tissue; the jaw assembly comprising a stationary first jaw portion and a second jaw portion pivotable about a jaw axis with respect to the first jaw portion between a closed position and an open position, the jaw assembly being configured to hold a thread for the suture; the needle mechanism comprising a needle being configured for piercing the tissue and pulling the thread from the jaw assembly, and a carrying member pivotable, independently of the second jaw portion at least when the second jaw portion is in its closed position, at a first end thereof with respect to the first jaw portion.

The suture passer may further comprise a jaw actuator configured to control pivoting of the second jaw portion, and a carrier actuator configured to control pivoting of the carrier portion, independently of the jaw actuator. The suture passer may further comprise a handle mechanism configured to facilitate a user to selectively and independently operate the jaw and carrier actuators. The handle mechanism may be configured such that operation of the carrier actuator to pivot the carrying member to a closed position also operates the jaw actuator to pivot the second jaw portion to its closed position.

The jaw assembly may further comprise a pivoting arrangement configured to facilitate hingedly articulating the first and second jaw portions, the pivoting arrangement being free of a member traversing the jaw assembly parallel to the jaw axis.

The pivoting arrangement may comprise axially spaced hinge members and corresponding sockets for receiving and permitting rotation therein of the hinge members. The hinge members may project from a proximal end of the second jaw portion.

The needle may be hingedly articulated to a second end of the carrying member between an open position in which it is disposed substantially perpendicular to the carrying member and a closed position in which it is disposed substantially parallel thereto.

The suture passer may further comprise a closing arrangement configured to bring the needle to its closed position when the carrying member is pivoted toward the jaw assembly. The jaw assembly may constitute a portion of the closing arrangement.

The needle mechanism may further comprise a biasing member configured to urge the needle to its open position.

The needle, in its closed position, may lie in registration with the carrying member.

The needle may be further hingedly articulated to a second end of the carrying member between an extended position in which it is disposed distally to the carrying member along a longitudinal axis thereof, an open position in which it is disposed substantially perpendicular to the carrying member, the needle mechanism further comprising a positioning element configured to urge the needle from its extended position to its open position, the biasing member and positioning element being configured to maintain the needle in its open position.

The positioning element may comprise a flat spring.

The needle mechanism may further comprise a locking arrangement configured to selectively impede pivoting of the needle when in its open position.

The locking arrangement may comprise facing cooperating surfaces of the needle and carrying members, the surfaces being configured to be selectively engaged with each other to impede the pivoting of the needle. The cooperating surfaces may be planar. The cooperating surfaces may be formed with non-planar surfaces. One of the cooperating surfaces may comprise a projection, with the other of the cooperating surfaces comprising a corresponding aperture configured to receive it when the needle is in its open position.

The needle may comprise an oblong aperture receiving a pin therewithin, configured to facilitate the needle to be displaced longitudinally, when in its open position, toward the carrying member, thereby engaging the cooperating surfaces.

One of the jaw portions may be formed, on a surface facing the other jaw portion, with a transverse groove for holding the thread. The jaw portion formed with the groove and the needle assembly may be disposed on opposite sides of the other jaw portion (i.e., the other jaw portion may be disposed between, on one side, the jaw portion formed with the groove and, on the other side, the needle assembly.) A surface of the other jaw portion facing the needle assembly is formed with a seat configured to at least partially receive therein the needle assembly.

The first jaw portion may be formed with the groove.

The first and second jaw portions may each be formed with a longitudinal slot, configured to allow passage therethrough of the needle, for example in its open position.

According to a further aspect of the presently disclosed subject matter, there is provided a suture passer defining a longitudinal axis and comprising a jaw assembly configured to be operated to selectively grip an internal tissue of a patient, and a needle mechanism configured to be operated to place a suture on the tissue; the jaw assembly comprising a stationary first jaw portion and a second jaw portion pivotable about a jaw axis with respect to the first jaw portion between a closed position and an open position, the jaw assembly further comprising a pivoting arrangement configured to facilitate hingedly articulating the first and second jaw portions, the pivoting arrangement being free of a member traversing the jaw assembly parallel to the jaw axis, the jaw assembly being configured to hold a thread for the suture; the needle mechanism comprising a needle being configured for piercing the tissue and pulling the thread from the jaw assembly, and a carrying member pivotable at a first end thereof with respect to the first jaw portion.

The pivoting arrangement may comprise axially spaced hinge members and corresponding sockets for receiving and permitting rotation therein of the hinge members. The hinge members may project from a proximal end of the second jaw portion.

The carrying member may be pivotable independently of the second jaw portion at least when the second jaw portion is in its closed position.

The suture passer may further comprise a jaw actuator configured to control pivoting of the second jaw portion, and a carrier actuator configured to control pivoting of the carrier portion, independently of the jaw actuator. The suture passer may further comprise a handle mechanism configured to facilitate a user to selectively and independently operate the jaw and carrier actuators. The handle mechanism may be configured such that operation of the carrier actuator to pivot the carrying member to a closed position also operates the jaw actuator to pivot the second jaw portion to its closed position.

The needle may be hingedly articulated to a second end of the carrying member between an open position in which it is disposed substantially perpendicular to the carrying member and a closed position in which it is disposed substantially parallel thereto.

The suture passer may further comprise a closing arrangement configured to bring the needle to its closed position when the carrying member is pivoted toward the jaw assembly. The jaw assembly may constitute a portion of the closing arrangement.

The needle mechanism may further comprise a biasing member configured to urge the needle to its open position.

The needle, in its closed position, may lie in registration with the carrying member.

The needle may be further hingedly articulated to a second end of the carrying member between an extended position in which it is disposed distally to the carrying member along a longitudinal axis thereof, an open position in which it is disposed substantially perpendicular to the carrying member, the needle mechanism further comprising a positioning element configured to urge the needle from its extended position to its open position, the biasing member and positioning element being configured to maintain the needle in its open position.

The positioning element may comprise a flat spring.

The needle mechanism may further comprise a locking arrangement configured to selectively impede pivoting of the needle when in its open position.

The locking arrangement may comprise facing cooperating surfaces of the needle and carrying members, the surfaces being configured to be selectively engaged with each other to impede the pivoting of the needle. The cooperating surfaces may be planar. The cooperating surfaces may be formed with non-planar surfaces. One of the cooperating surfaces may comprise a projection, with the other of the cooperating surfaces comprising a corresponding aperture configured to receive it when the needle is in its open position.

The needle may comprise an oblong aperture receiving a pin therewithin, configured to facilitate the needle to be displaced longitudinally, when in its open position, toward the carrying member, thereby engaging the cooperating surfaces.

One of the jaw portions may be formed, on a surface facing the other jaw portion, with a transverse groove for holding the thread. The jaw portion formed with the groove and the needle assembly may be disposed on opposite sides of the other jaw portion (i.e., the other jaw portion may be disposed between, on one side, the jaw portion formed with the groove and, on the other side, the needle assembly.) A surface of the other jaw portion facing the needle assembly is formed with a seat configured to at least partially receive therein the needle assembly.

The first jaw portion may be formed with the groove.

The first and second jaw portions may each be formed with a longitudinal slot, configured to allow passage therethrough of the needle, for example in its open position.

According to a still further aspect of the presently disclosed subject matter, there is provided a suture passer defining a longitudinal axis and comprising a jaw assembly configured to be operated to selectively grip an internal tissue of a patient, and a needle mechanism configured to be operated to place a suture on the tissue; the jaw assembly comprising a stationary first jaw portion and a second jaw portion pivotable about a jaw axis with respect to the first jaw portion between a closed position and an open position, the jaw assembly being configured to hold a thread for the suture; the needle mechanism comprising a needle being configured for piercing the tissue and pulling the thread from the jaw assembly, and a carrying member pivotable at a first end thereof with respect to the first jaw portion, the needle being hingedly articulated to a second end thereof between an open position in which it is disposed substantially perpendicular to the carrying member and a closed position in which it is disposed substantially parallel thereto.

The suture passer may further comprise a closing arrangement configured to bring the needle to its closed position when the carrying member is pivoted toward the jaw assembly. The jaw assembly may constitute a portion of the closing arrangement.

The needle mechanism may further comprise a biasing member configured to urge the needle to its open position.

The needle, in its closed position, may lie in registration with the carrying member.

The needle may be further hingedly articulated to a second end of the carrying member between an extended position in which it is disposed distally to the carrying member along a longitudinal axis thereof, an open position in which it is disposed substantially perpendicular to the carrying member, the needle mechanism further comprising a positioning element configured to urge the needle from its extended position to its open position, the biasing member and positioning element being configured to maintain the needle in its open position.

The positioning element may comprise a flat spring.

The needle mechanism may further comprise a locking arrangement configured to selectively impede pivoting of the needle when in its open position.

The locking arrangement may comprise facing cooperating surfaces of the needle and carrying members, the surfaces being configured to be selectively engaged with each other to impede the pivoting of the needle. The cooperating surfaces may be planar. The cooperating surfaces may be formed with non-planar surfaces. One of the cooperating surfaces may comprise a projection, with the other of the cooperating surfaces comprising a corresponding aperture configured to receive it when the needle is in its open position.

The needle may comprise an oblong aperture receiving a pin therewithin, configured to facilitate the needle to be displaced longitudinally, when in its open position, toward the carrying member, thereby engaging the cooperating surfaces.

One of the jaw portions may be formed, on a surface facing the other jaw portion, with a transverse groove for holding the thread. The jaw portion formed with the groove and the needle assembly may be disposed on opposite sides of the other jaw portion (i.e., the other jaw portion may be disposed between, on one side, the jaw portion formed with the groove and, on the other side, the needle assembly.) A surface of the other jaw portion facing the needle assembly is formed with a seat configured to at least partially receive therein the needle assembly.

The first jaw portion may be formed with the groove.

The first and second jaw portions may each be formed with a longitudinal slot, configured to allow passage therethrough of the needle, for example in its open position.

The jaw assembly may further comprise a pivoting arrangement configured to facilitate hingedly articulating the first and second jaw portions, the pivoting arrangement being free of a member traversing the jaw assembly parallel to the jaw axis.

The pivoting arrangement may comprise axially spaced hinge members and corresponding sockets for receiving and permitting rotation therein of the hinge members. The hinge members may project from a proximal end of the second jaw portion.

The carrying member may be pivotable independently of the second jaw portion at least when the second jaw portion is in its closed position.

The suture passer may further comprise a jaw actuator configured to control pivoting of the second jaw portion, and a carrier actuator configured to control pivoting of the carrier portion, independently of the jaw actuator. The suture passer may further comprise a handle mechanism configured to facilitate a user to selectively and independently operate the jaw and carrier actuators. The handle mechanism may be configured such that operation of the carrier actuator to pivot the carrying member to a closed position also operates the jaw actuator to pivot the second jaw portion to its closed position.

According to a still further aspect of the presently disclosed subject matter, there is provided a suture passer according to any of the above aspects, comprising a handle mechanism according to the below aspect.

According to a still further aspect of the presently disclosed subject matter, there is provided a suture passer according to any of the above aspects, comprising a handle mechanism according to the below aspect.

According to a still further aspect of the presently disclosed subject matter, there is provided a handle mechanism for a suture passer, the suture passer having a suturing mechanism for placement of a suture on a patient, the suturing mechanism comprising a jaw portion for gripping an internal tissue of a patient and moveable between open and closed positions, and a needle mechanism moveable between open and closed positions and having a moveable carrying member for deploying a needle to place the suture, the suture passer further comprising a handle mechanism configured to facilitate independent operation of the jaw portion and the carrying member; the handle mechanism comprising a trigger assembly comprising a jaw lever configured to operate the jaw portion to move it between its respective open and closed positions, and a carrier lever configured to operate the carrying member to move it between its respective open and closed positions; the trigger assembly being configured such that engagement of the carrier lever to move the carrying member to its closed position engages the jaw lever to move the jaw portion to its closed position, and being further configured such that the carrier lever may be released to autonomously bring the carrying member to its open position with the jaw portion remaining in its closed position.

The trigger assembly may further comprise jaw and carrier biasing elements configured to urge, respectively, the jaw and carrier levers into positions associated with open positions of the jaw portion and the carrying member.

The trigger assembly may further comprise a coupling element configured to engage the jaw and carrier levers to move in tandem with each other, and to be selectively disengaged to permit independent movement of the jaw and carrier levers.

The trigger assembly may be configured to allow autonomous re-engagement of the coupling element with the jaw and carrier levers.

The trigger assembly may further comprise a carrier-release button for activation by a user, wherein activation of the carrier-release button disengages the coupling element.

The trigger assembly may further comprise a ratchet mechanism configured, when engaged, to allow the jaw lever to be moved to a position associated with the closed position of the jaw portion, and prevent movement thereof to a position associated with the open position of the jaw portion.

The ratchet mechanism may comprise a release element configured to disengage the ratchet mechanism, thereby allowing autonomous movement of the jaw lever to a position associated with the open position of the jaw portion.

The release element may comprise a jaw-release button configured for activation by a user, wherein activation of the jaw-release button disengages the ratchet mechanism.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which.

DETAILED DESCRIPTION

Figure 1:
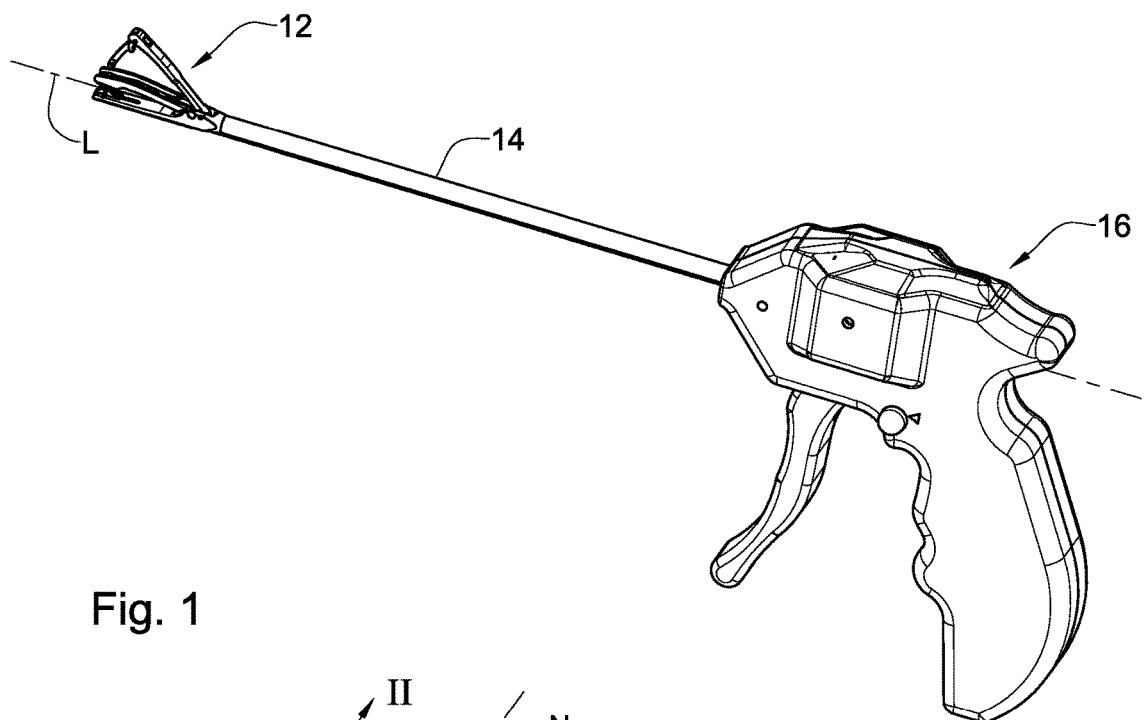
FIG. 1 is a perspective view of a suture passer according to the presently disclosed subject matter.

As illustrated in FIG. 1, there is provided a suture passer, which is generally indicated at 10, for percutaneous placement of a suture on internal tissue of a patient. The suture passer 10 comprises a suturing mechanism 12 on a distal end of a cannula 14 defining a longitudinal axis L. The cannula 14 is mounted at a proximal end thereof to a handle assembly 16, which is configured to facilitate a user to operate the suturing mechanism 12, as will be described herein below.

Figure 2A:
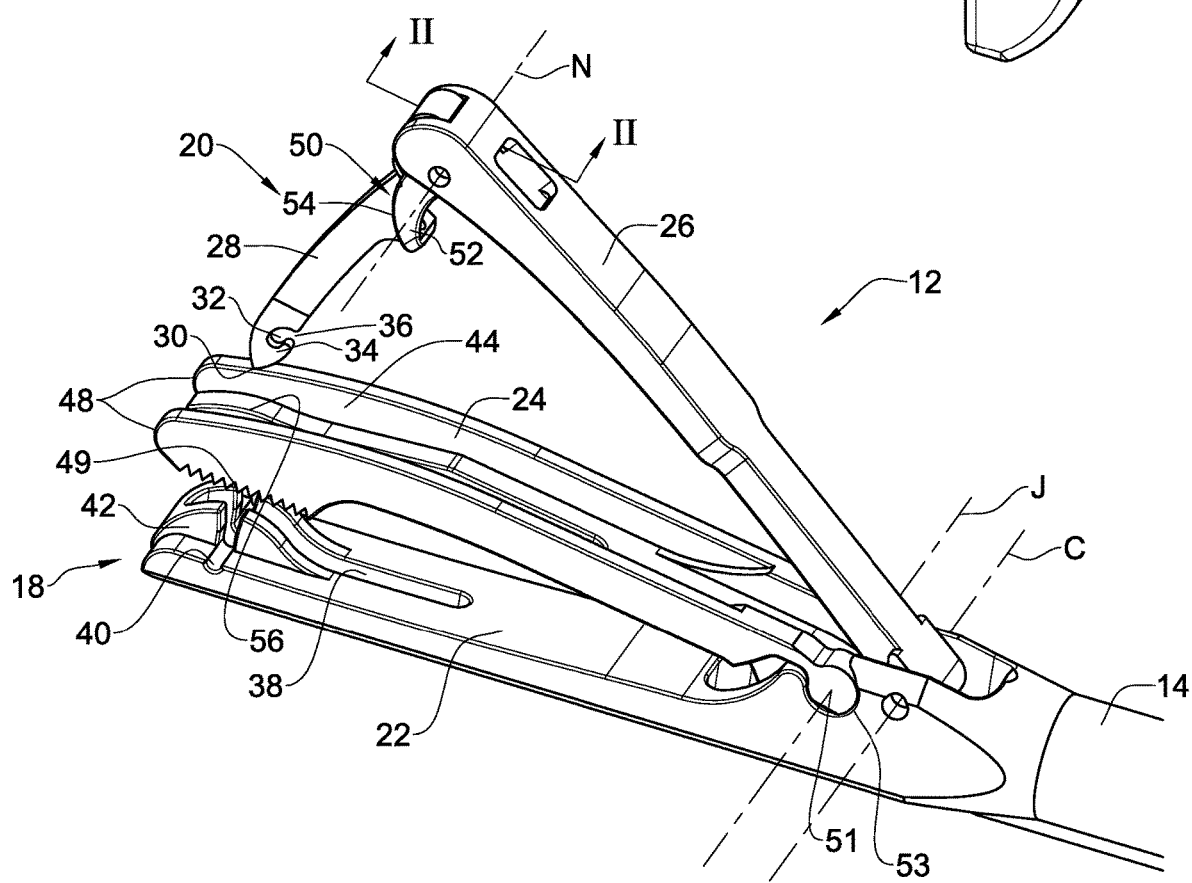
FIGS. 2A and 2B are top-rear and bottom-front perspective views, respectively, of a suturing mechanism of the suture passer illustrated in FIG. 1.
Figure 2B:
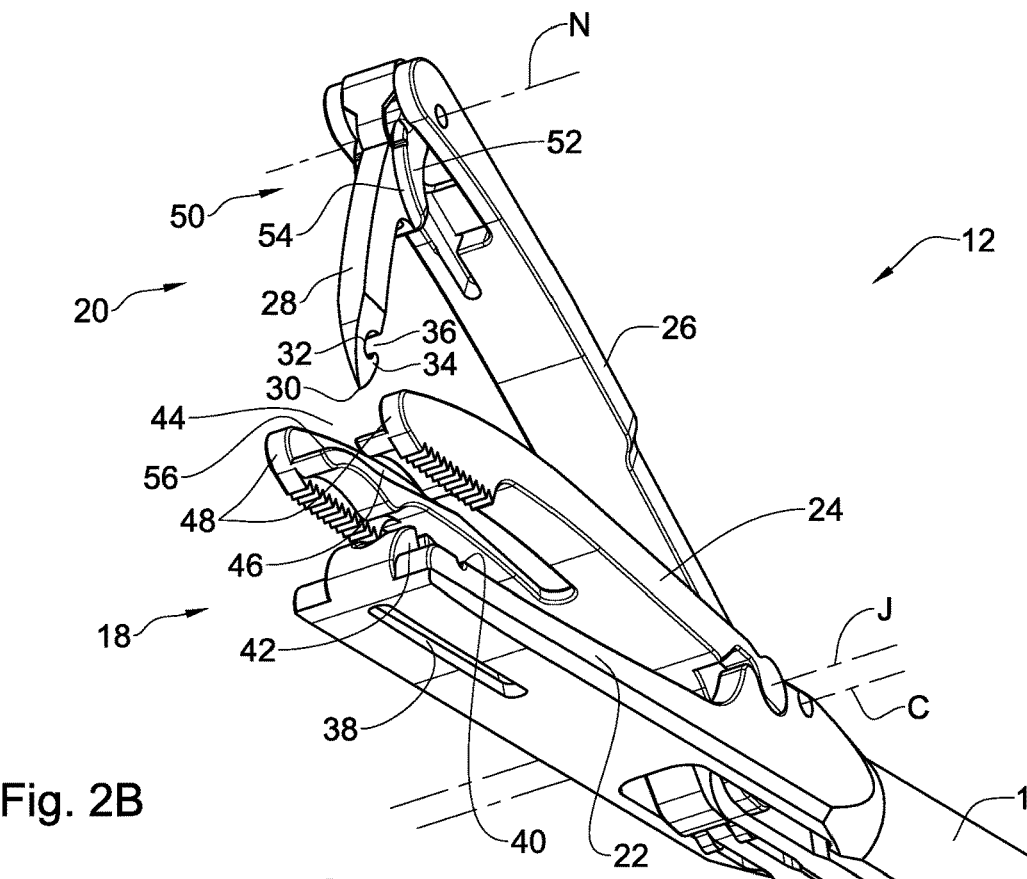

As illustrated in FIGS. 2A and 2B, the suturing mechanism 12 comprises a jaw assembly 18 and a needle mechanism 20. The jaw assembly comprises a lower jaw portion 22 and an upper jaw portion 24 hingedly articulated, at a distal end thereof, with respect to the lower jaw portion, e.g., to the cannula 14, through jaw axis J between an open-jaw position and a closed-jaw position (wherein FIGS. 2A and 2B show the upper jaw portion 24 is a partially open-jaw position). The lower jaw portion 22 may be stationary, for example being formed as part of the cannula 14.

It will be appreciated that in the presently disclosed subject matter and appended claims, the terms "upper" and "lower," as well as related and other terms which indicate direction and/or orientation, are used with respect to the example illustrated in and described with reference to the accompanying drawings, and should not be construed as limiting, e.g., to a particular orientation.

The needle mechanism 20 comprises an carrying member 26 and a needle 28 hingedly articulated, at a proximal end thereof, to a distal end of the carrying member through needle axis N between an open-needle position, in which the needle is disposed substantially perpendicular to the carrying member, and a closed-needle position (wherein the open-needle position is illustrated in FIGS. 2A and 2B), in which the needle lies in registration with the carrying member. It will be appreciated that the description herein and in the accompanying claims of the needle 28, in its open-needle position, being substantially perpendicular to the carrying member 26 is not to be construed as being limited to a perfect right angle, but rather that it projects therefrom in a transverse direction, which may deviate from a right angle by any suitable amount which still allowing the needle to function for suture placement, as will be described below.

The proximal end of the carrying member 26 is hingedly articulated to the cannula 14 through carrying axis C between an open-carrier position and a closed-carrier position (wherein the open-carrier position is illustrated in FIGS. 2A and 2B). A biasing member (not illustrated), such as a torsion or other suitable spring, may be provided to urge the needle 28 into its open-needle position. According to some examples, the distal end of the carrying member 26 may be formed so as to limit the pivoting of the needle 28 to about 90° therewith.

It will be appreciated that some or all of the axes J, N, C may be parallel to one another, and perpendicular to the longitudinal axis L.

The needle 28 comprises a distally located tip 30, configured to puncture the tissue to be sutured, and an eye 32. The eye 32 is partially defined by a proximally-directed hook 34, disposed below (distally to) an opening 36 to the eye.

As the upper jaw portion 24 may pivot between open- and closed-jaw positions, references in the present description to the carrier position describe the disposition of the carrying member 26 with respect to the upper jaw portion. For example, when the upper jaw portion 24 is in its open-jaw position, the carrying member 26 is considered to be in its closed-carrier position when it is disposed against the upper jaw portion, even though it is spaced from the lower jaw portion 22.

The lower jaw portion 22 is formed with a through-going lower slot 38, extending generally in the direction of the length of the cannula 14 (i.e., perpendicularly to the needle and/or carrier axis N, C. The width of the lower slot 38 is sufficient to receive therethrough the needle 28, e.g., when in the open-needle position with the carrying member in the closed-carrier position.

An upper surface of the lower jaw portion 22 is formed with a groove 40, configured to receive therein a thread for forming the suture, before the cannula 14 is inserted into the patient, as will be described below. The groove 40 extends substantially perpendicularly to the lower slot 38.

The upper surface of the lower jaw portion 22 is further formed with a protrusion 42 extending toward the upper jaw portion 24. The protrusion 42 is divided into four portions by the lower slot 38 and the groove 40.

An upper surface of the upper jaw portion 24 is provided with a seat 44 (e.g., formed as a depression therein) configured to receive therein the carrying member 26 when in its closed-carrier position. According to some examples, the seat 44 is formed such that top surfaces of the carrying member 26 and upper jaw portion 24 are flush when the carrying member is received therein.

The upper jaw portion 24 is further formed with an upper slot 46, formed generally parallelly to the length of the cannula 14, giving rise to two parallel prongs 48 extending generally in the direction of the length of the cannula 14. The width of the upper slot 46 is sufficient to receive therethrough the needle 28, e.g., when in the open-needle position with the carrying member in the closed-carrier position. In addition, the upper slot 46 is of a sufficient length so as to accommodate the needle 28 when in the closed-needle position, when the carrying member 26 is received within the seat 44. Consequently, the upper slot 46 allows the needle 28 to shift between its open- and closed-needle positions without interference of the upper jaw portion 24, irrespective of its relative positions with the carrying member 26.

The upper jaw portion 24 is further formed with clamping elements 49, for example near the distal ends of the prongs 48, configured to cooperate with the lower jaw portion 22, e.g., with the protrusion 42 thereof, to facilitate the jaw assembly 18 gripping the tissue during operation. The clamping elements 49 may comprise a plurality of lateral teeth as illustrated, or any other suitable features, including, but not limited to, spikes, knurling, etc.

The upper jaw portion 24 may be configured to pivot without a pin or other similar element traversing (i.e., passing therethrough) the jaw axis J. Accordingly, the proximal end thereof may comprise two axially spaced hinge member 51, such as knobs, e.g., projecting proximally therefrom, each received and configured for rotation within a corresponding socket 53 formed within the lower jaw portion 22 at a proximal end thereof. This arrangement facilitates pivoting of the upper jaw portion 24 independently of the carrying member 26, as the absence of a pin or other similar element along and/or parallel to the jaw axis J permits the carrying member to pivot freely. The hinge member 51 and sockets 53 constitute a pivoting arrangement of the jaw assembly 18.

It will be appreciated that while the lower and upper slots 38, 46 are described herein with reference to and illustrated in the accompanying figures as being, respectively, closed and open at distal ends thereof, this is not to be construed as limiting. The suture passer 10 may be provided with the lower slot 38 being open at its distal end, the upper slot 46 being closed at its distal end, both being closed or both being open at their distal ends, etc., without departing from the scope of the presently disclosed subject matter, mutatis mutandis.

It will further be appreciated that features described herein with reference to and illustrated in the accompanying figures as being provided, respectively, on the lower and upper jaw portions 22, 24, may be provided on the other jaw portion, without departing from the scope of the presently disclosed subject matter, mutatis mutandis.

The needle 28 and upper jaw portion 24 may comprise a closing arrangement, indicated at 50, configured to bring the needle to its closed-needle position when the carrying member 26 is brought to its closed carrying position. The closing arrangement 50 may comprise a follower 52 provided on the needle 28, e.g., at its proximal end, for example adjacent the needle axis N. The curved surface 54 of the follower is disposed so as to bear upon an upper surface 56 of the seat 44 formed in the upper jaw portion 24, constituting a cam surface of the closing arrangement 50, thereby biasing the needle to its closed-needle position when the carrying member 26 is fully brought into its closed-carrier position. It will be appreciated that as the follower 52 is disposed at the proximal end of the needle 28, the carrying member 26 may be brought partially into its closed-carrier position without engaging the closing arrangement 50, i.e., the needle may remain in its open-needle position until the carrying member has been almost fully brought into its closed-carrier position.

Figure 2C:
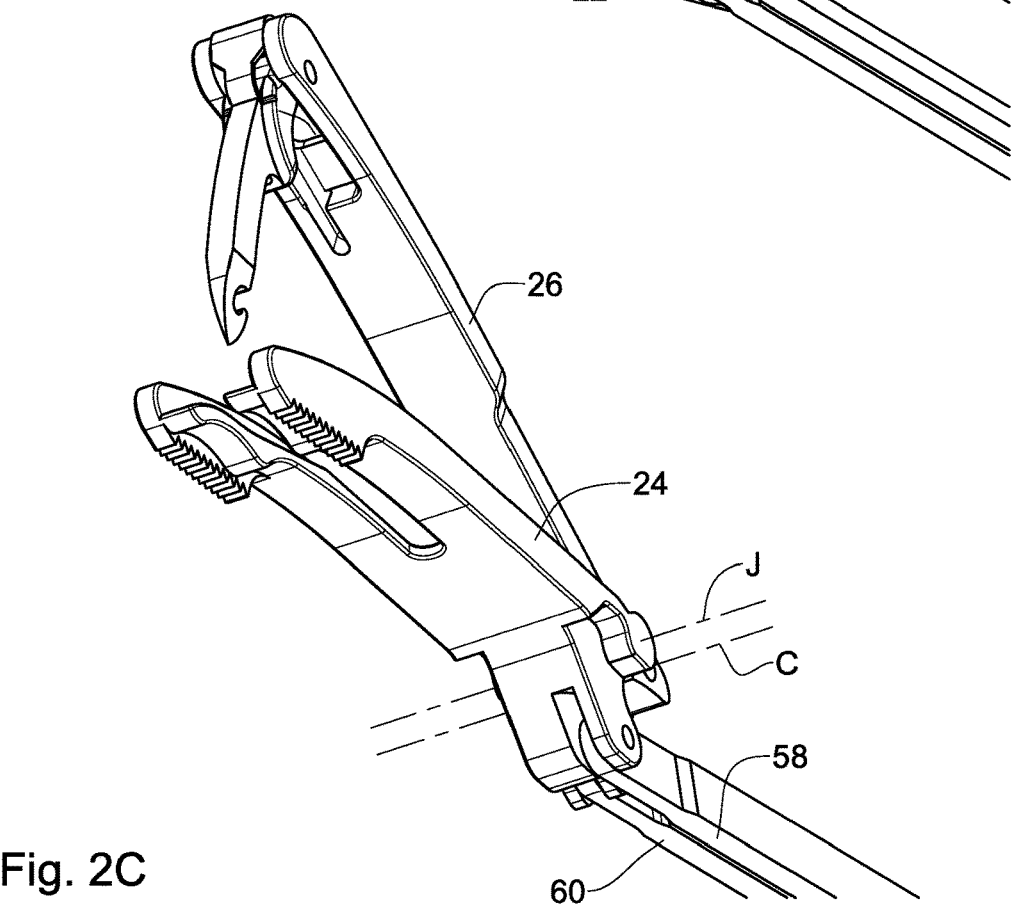
FIG. 2C is the view of FIG. 2B, with a cannula of the suture passer removed.

As best seen in FIG. 2C, the suture passer 10 further comprises a jaw actuator 58 and a carrier actuator 60 extending from the handle assembly 16 to the suturing mechanism 12 through the cannula 14 (hidden in FIG. 2C). The jaw actuator 58 is hingedly connected to a proximal end of the upper jaw portion 24, e.g., proximal to the jaw axis J, such that longitudinal displacement thereof activates the upper jaw portion to pivot about the jaw axis between its open- and closed-jaw positions. Similarly, the carrier actuator 60 is hingedly connected to a proximal end of the carrying member 26, e.g., proximal to the carrier axis C, such that longitudinal displacement thereof activates the carrying member to pivot about the carrier axis between its open- and closed-carrier positions.

The handle assembly 16 is configured to facilitate operation of the elements of the suturing mechanism 12 individually, i.e., allowing the upper jaw portion 24 to be brought into its open-jaw position, and bringing the carrying member 26 into its open-carrier and closed-carrier positions without affecting the upper jaw portion, e.g., allowing it to remain in its closed-jaw position.

Figure 3B:
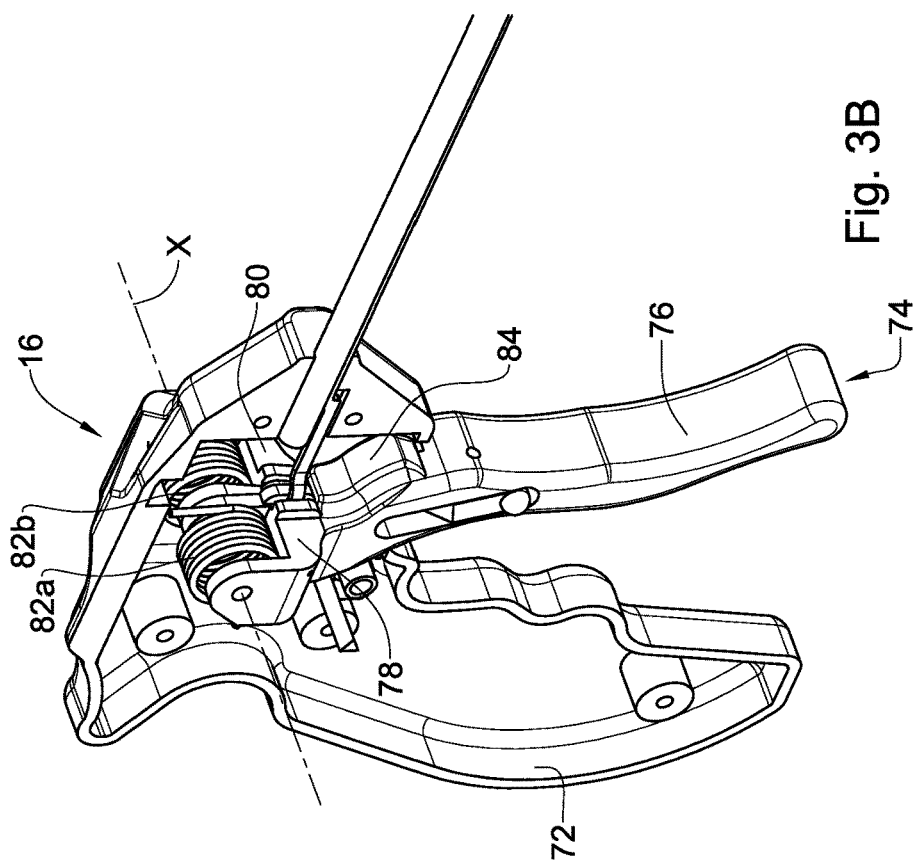
FIGS. 3A and 3B are perspective views of opposite sides of a handle assembly with a trigger assembly of the suture passer illustrated in FIG. 1, each with a portion of a housing thereof removed.
Figure 3A:
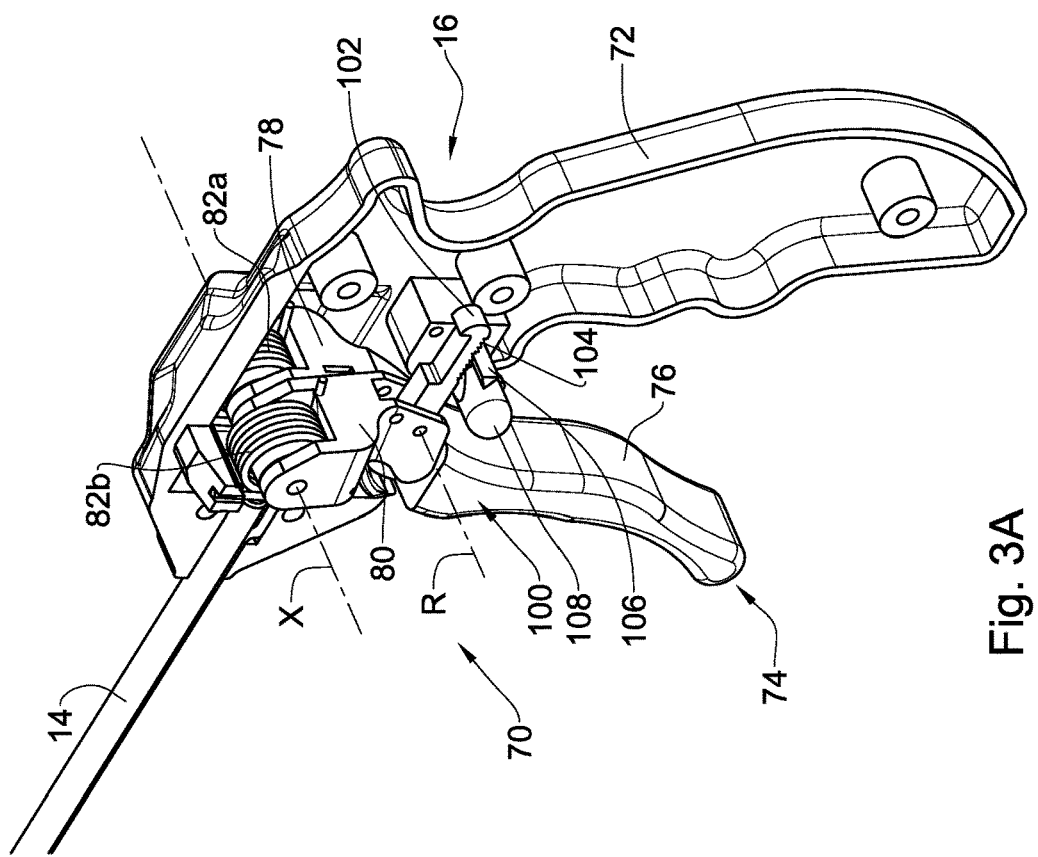

As illustrated in FIG. 3, the handle assembly 16 comprises a trigger assembly, which is generally indicated at 70, inside a housing 72 (only part of which is illustrated in FIG. 3).

The trigger assembly 70 comprises a main trigger 74 formed with a downwardly projecting handgrip 76 and an upper carrier lever 78 configured to move in tandem as a single element, and further comprises a jaw lever 80. The carrier and jar levers 78, 80 may be pivotally mounted about a common axis X, disposed at an upper end thereof. Biasing elements 82a, 82b associated with each of the levers 78, 80 are provided to bias each forwardly into respective released positions thereof.

It will be appreciated that in the presently disclosed subject matter and appended claims, the terms "forward" and "rearward," as well as related and similar terms, are used in connection with the handle assembly 16 with reference to an orientation wherein the forward direction indicates one which is toward the suturing mechanism 12, and the rearward direction is opposite thereto.

The carrier lever 78 is connected to the carrier actuator 60, such that engagement thereof displaces the carrier actuator proximally, thereby urging the carrying member 26 toward its closed-carrier position. Similarly, the jaw lever 80 is connected to the jaw actuator 58, such that engagement thereof displaces the jaw actuator proximally, thereby urging the upper jaw portion 24 toward its closed-jaw position.

The trigger assembly 70 may be configured such that pivoting the main trigger 74 into its engaged position also engages the jaw lever 80, while the main trigger may be released without releasing the jaw lever. Accordingly, the main trigger may comprise a barrier 84 disposed in front of (i.e., closer to the suturing mechanism 12) configured to bear upon the jaw lever 80 when the main trigger 74 is engaged. Thus, engagement of the main trigger 74 causes the barrier 84 to engage the jaw lever 80 as well, while releasing the main trigger merely results in the barrier moving in a forward direction away from the jaw lever, without affecting its position. Accordingly, engaging the main trigger 74, i.e., by depressing the handgrip 76 thereof, brings the main jaw portion 24 and the carrying member 26 into their respective closed positions, while releasing only the main trigger brings the carrying member into its open-carrier position, while the upper jaw portion remains in its closed-jaw position.

Figure 4A:
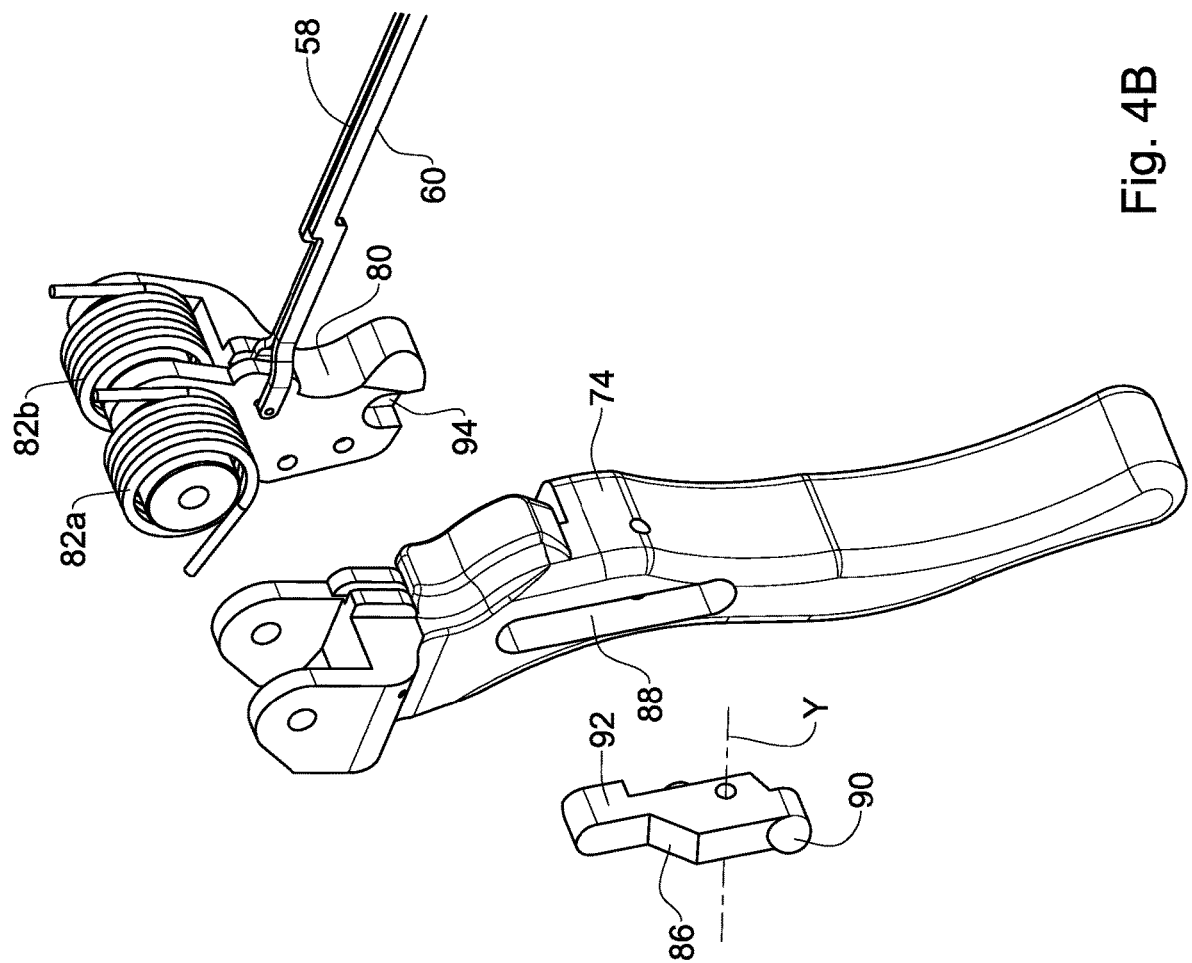
FIG. 4A is a perspective view of a portion of the trigger assembly illustrated in FIGS. 3A and 3B.
Figure 4B:
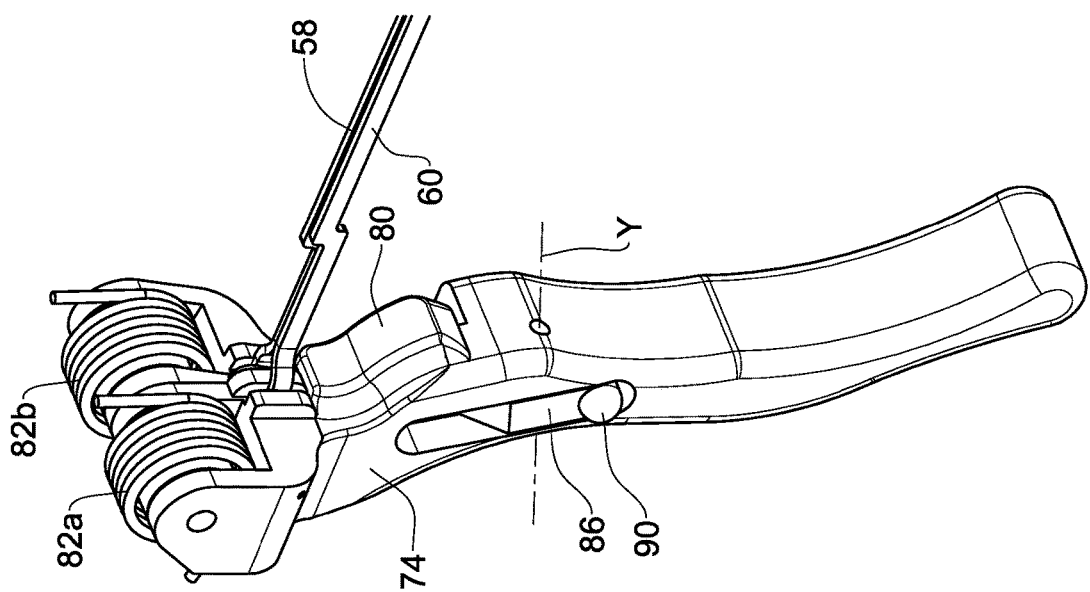
FIG. 4B is a partially exploded view of the portion of the trigger assembly illustrated in FIG. 4A.

The main trigger 74 and jaw lever 80 may be configured to engage with one another to move in tandem, and to be selectively disengaged to move independently from one another. As illustrated in FIGS. 4A and 4B, the trigger assembly 70 may comprise a coupling element 86 received within a slot 88 formed in the main trigger 74, e.g., in the handgrip 76 thereof, and configured to pivot about an axis Y. A carrier-release button 90, formed at a lower end thereof, projects from the side of the main trigger 74 for engagement by a user. A biasing element (not illustrated) such as a spring, is provided opposite the carrier-release button 90, configured to urge it outwardly.

Figure 4C:
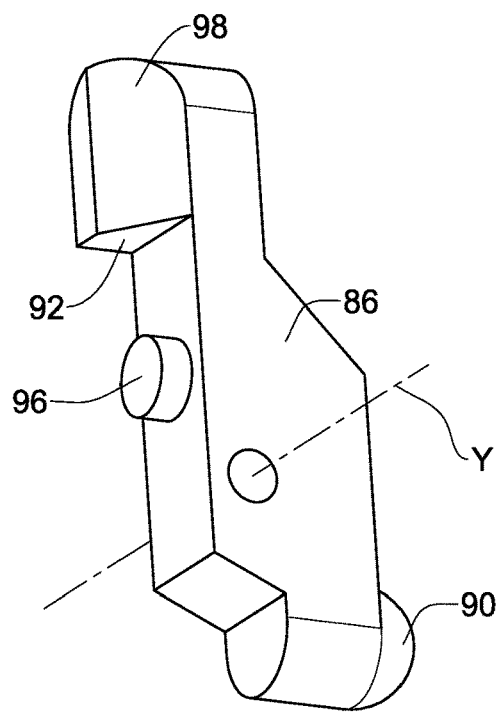
FIG. 4C is a perspective view of a coupling element of the trigger assembly, from an opposite perspective view of that in FIGS. 4A and 4B.

The coupling element 86 further comprises a tab 92 formed at its upper end, projecting toward the jaw lever 80 and received within an indent 94 formed therewithin. When the tab 92 is received within the indent 94, the coupling element 86 is engaged with the main trigger 74 and the jaw lever 80, facilitating their movement (or being held in place) in tandem with one another. Depression of the carrier-release button 90 causes the coupling element 86 to pivot about the axis Y, thereby removing the tab 92 from the indent 94, disengaging the main trigger 74 from the jaw lever 80. As illustrated in FIG. 4C, the inwardly-facing surface of the coupling element 86 comprises a bulge 96 protruding therefrom, constituting a fulcrum to facilitate the pivoting of the coupling element.

As further illustrated in FIG. 4C, an inwardly-facing surface 98 of the tab 92 is formed sloping rearwardly (i.e., decreases in size in a rearward direction). Accordingly, when the jaw lever 80 is in rearwardly disposed with respect to the main trigger 74, wherein the tab 92 is removed from the indent 94, a forward pivoting of the jaw lever will cause it to bear upon the sloped surface 98 of the tab, biasing it out of its way until the tab is aligned with the indent. The biasing element provided opposite the carrier-release button 90 urges the tab 92 into the indent 94 when they are aligned, thereby re-engaging the main trigger 74 and the jaw lever 80. Accordingly, when the jaw lever 80 is urged toward the main trigger 74, no user intervention is required to re-engage them, and the coupling element 86.

Figure 5:
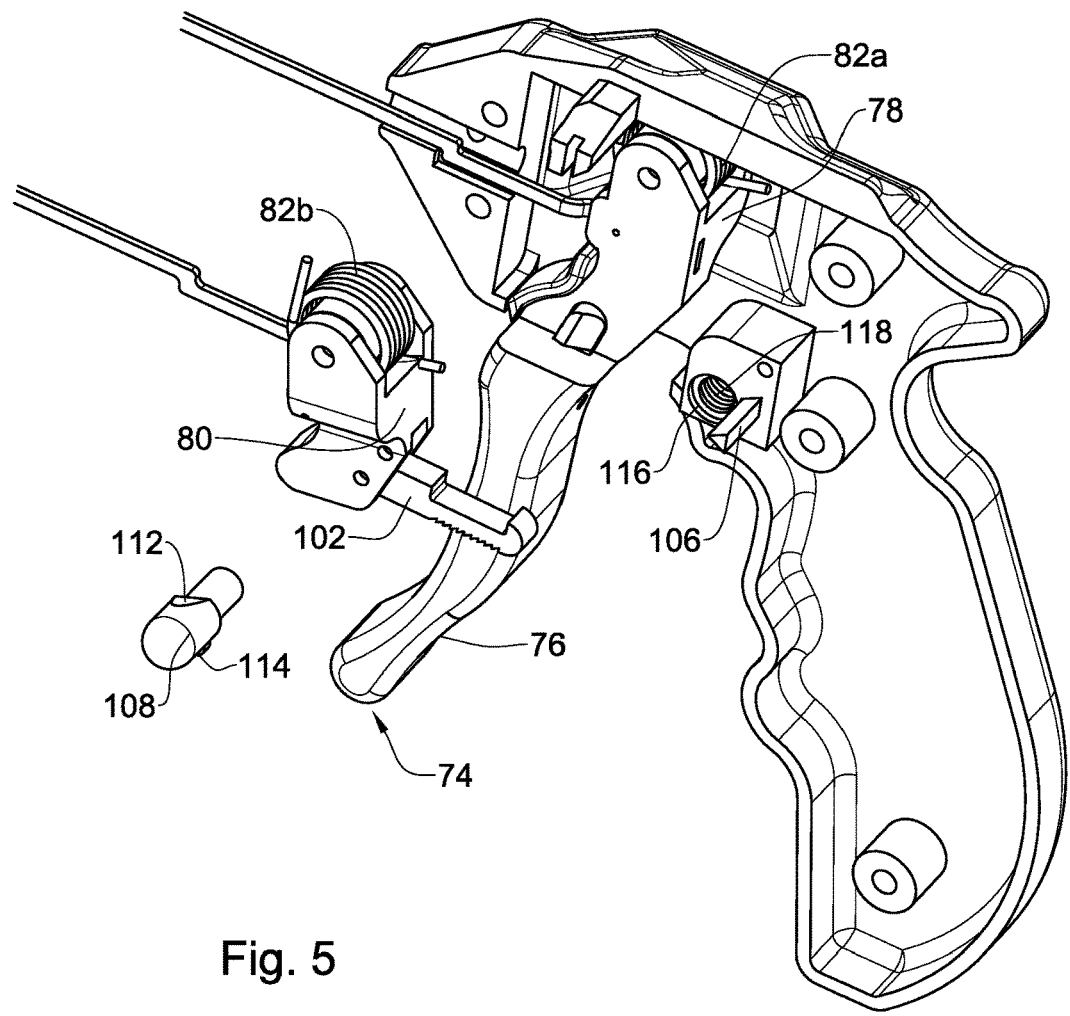
FIG. 5 is a partially exploded view of the handle assembly as illustrated in FIG. 3A.

The jaw lever 80 may be configured to be secured in a rearward position, and selectively released therefrom to return, e.g., autonomously (i.e., without the need for the user to manually operate it), to a forward position. Reverting to FIG. 3A, and as illustrated in FIG. 5, the trigger assembly 70 may comprise a ratchet mechanism, generally indicated at 100, associated with the jaw lever 80. The ratchet mechanism 100 comprises a rack 102 formed with a plurality of downward-facing teeth 104, a fixed pawl 106, and a jaw-release button 108 disposed below the rack. The rack 102 is articulated at a forward end thereof to the jaw lever 80, and configured to pivot about an axis R. Accordingly, a biasing member 110, such as a spring, is provided to urge the rack 102 downwardly, i.e., such that the teeth 104 engage the pawl 106. The teeth 104 and the pawl 106 are designed (e.g., the slopes of the teeth and the orientation of the pawl) such that when they are engaged, the rack 102 may be advanced rearwardly (i.e., as indicated by arrow A), and prevented from returning forwardly.

The jaw-release button 108 is formed with an upper sloped surface 112 and a stopper 114. A first end thereof projects from a side of the housing 72, and a second end thereof is received within a well 116 formed within the opposing side of the housing. A biasing element 118, such as a spring, is provided within the well 116 to urge the jaw-release button 108 outwardly. The stopper 114 is disposed between an inner surface of the housing 72 and the well 116, limiting movement of the jaw-release button 108, thereby ensuring that it remains in place when not depressed.

The jaw-release button 108 is disposed such that depression thereof causes its sloped surface 112 to advance along a bottom surface of the rack 102, thereby lifting it and disengaging the teeth 104 from the pawl 106. As the jaw lever 80 is biased forwardly by biasing element 82b, the disengagement caused by depressing the jaw release button 108 results in the jaw lever, and with it the jaw actuator 58, autonomously returning to its forward position, thereby brining the upper jaw portion 24 to its open-jaw position.

In use, the handle assembly 16 may be employed by a user to control the operation of the suturing mechanism 12 using a single hand. When both the carrier lever 78 and the jaw lever 80 are in their forward positions, the carrying member 26 and the upper jaw portion 24 are in their respective open positions. Engagement of the handgrip 76 brings both the carrier lever 78 (by virtue of its tandem movement with the handgrip) and the jaw lever 80 (by virtue of its being borne upon by the barrier 84) into their rearward positions, against the bias of biasing elements 82a, 82b, displacing the carrier and jaw actuators 60, 58 rearwardly (i.e., proximally), and bringing the carrying member 26 and the upper jaw portion 24 into their respective closed positions, as described above. As the rack 102 of the ratchet mechanism 100 is connected to the jaw lever 80, it is moves rearwardly; engagement of the teeth 104 thereof with the pawl 106 prevent it from returning to its forward position, as described above. The coupling element 86 maintains engagement between the carrier lever 78 and the jaw lever 80 as described above, thereby preventing the carrier lever from returning to its forward position.

Engagement of (i.e., depressing) the carrier-release button 90 causes the coupling element 86 to disengage from the jaw lever 80, as described above, thereby disengaging the carrier lever 78 from the jaw lever 80. The carrier lever 78 is then returned to its forward position by its associated biasing element 82a, causing the carrying member 26 to assume its open-carrier position, while the upper jaw portion 24 remains in its closed-jaw position. The handgrip 76 may be re-engaged to return the carrying member 26 to its closed-carrier.

Engagement of (i.e., depressing) the jaw-release button 108 causes the teeth 104 of the rack 102 to disengage from the pawl 106, as described above. The jaw lever 80 is then returned to its forward position by its associated biasing element 82b, causing the upper jaw portion 24 to assume its open-jaw position. If the carrier lever 78 had been in its rearward position (i.e., the carrying member 26 has been in its closed-carrier position), it moves forwardly with the jaw lever 80, causing the carrying member to assume its open-carrier position.

As illustrated in FIGS. 6A through 6I, the suturing mechanism 12 described above with reference to FIGS. 2A through 3 may be used to place a suture on an internal tissue of a patient.

Figure 6A:
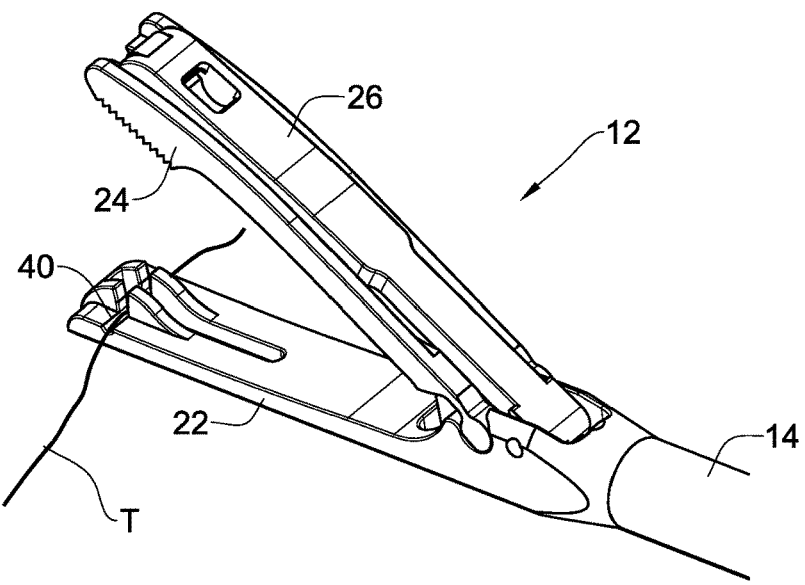
FIGS. 6A through 6I illustrate an example of operation of the suturing mechanism illustrated in FIGS. 2A through 2C.

As illustrated in FIG. 6A, prior to insertion of the suturing mechanism 12 into the patient, a thread T is placed within the groove 40 formed in the lower jaw portion 22, with the upper jaw portion 24 in its open-jaw position, and the carrying member 26 and needle 28 in their respective closed-carrier and needle positions.

Figure 6B:
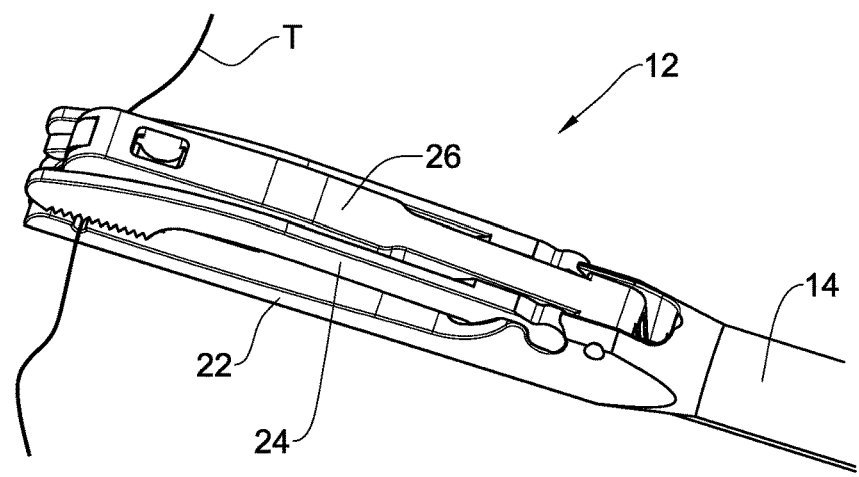

As illustrated in FIG. 6B, the upper jaw portion 24 is then activated to be brought into its closed-jaw position, with the carrying member 26 and needle 28 remaining in their closed positions. It will be appreciated that as the upper jaw portion 24, carrying member 26, and needle 28 are each in their respective closed positions, they are all disposed substantially parallel to the cannula 14, i.e., aligned with a path of insertion of the suturing mechanism 12 into the patient. This arrangement provides a small profile thereof, limiting the size of the opening required for insertion. The suturing mechanism 12 is inserted into the patient in the direction indicated by arrow A.

Figure 6C:
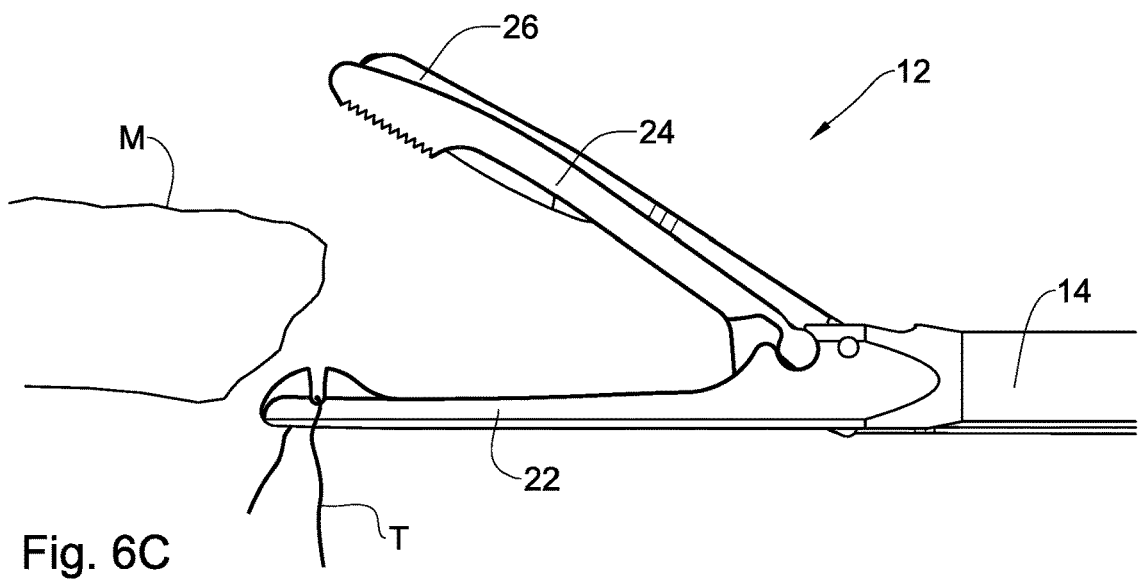

As illustrated in FIG. 6C, the suturing mechanism 12, once inserted into the patient, approaches the tissue M to be sutured. The upper jaw portion 24 is brought into its open-jaw position, while the carrying member 26 and needle 28 remain in their respective closed positions. The suturing mechanism 12 is advanced, in the direction indicated by arrow A, toward the tissue M, such that it is disposed within the jaw assembly (i.e., between the upper and lower jaw portions 24, 22).

Figure 6D:
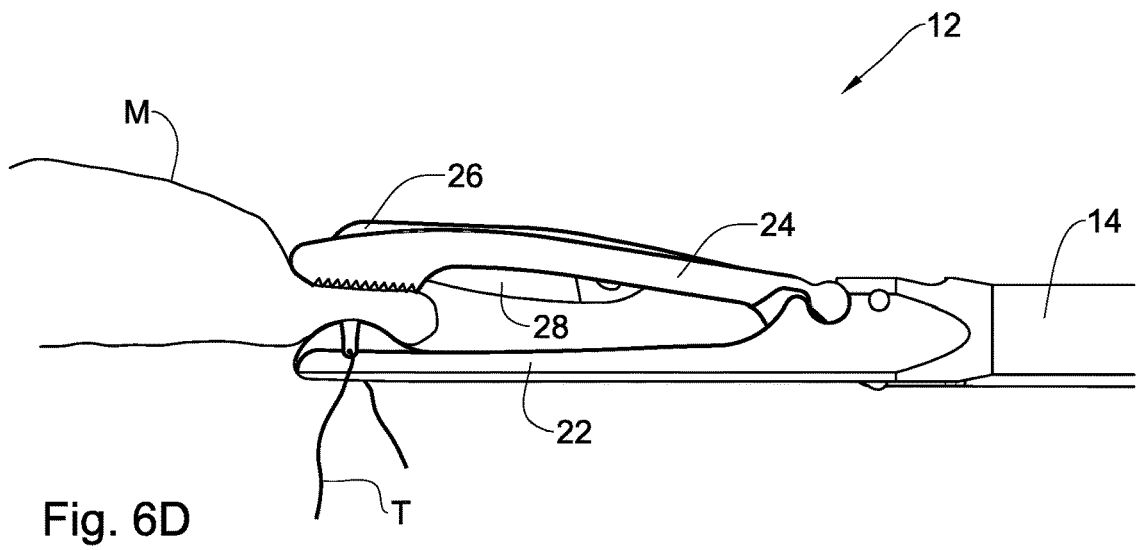

As illustrated in FIG. 6D, the upper jaw portion 24 is then brought into its closed-jaw position onto the tissue M, wherein the clamping elements 49 engage it to grip it, thereby facilitating keeping it in its position. It will be appreciated that at this stage, the thread T is disposed below the tissue M.

Figure 6E:
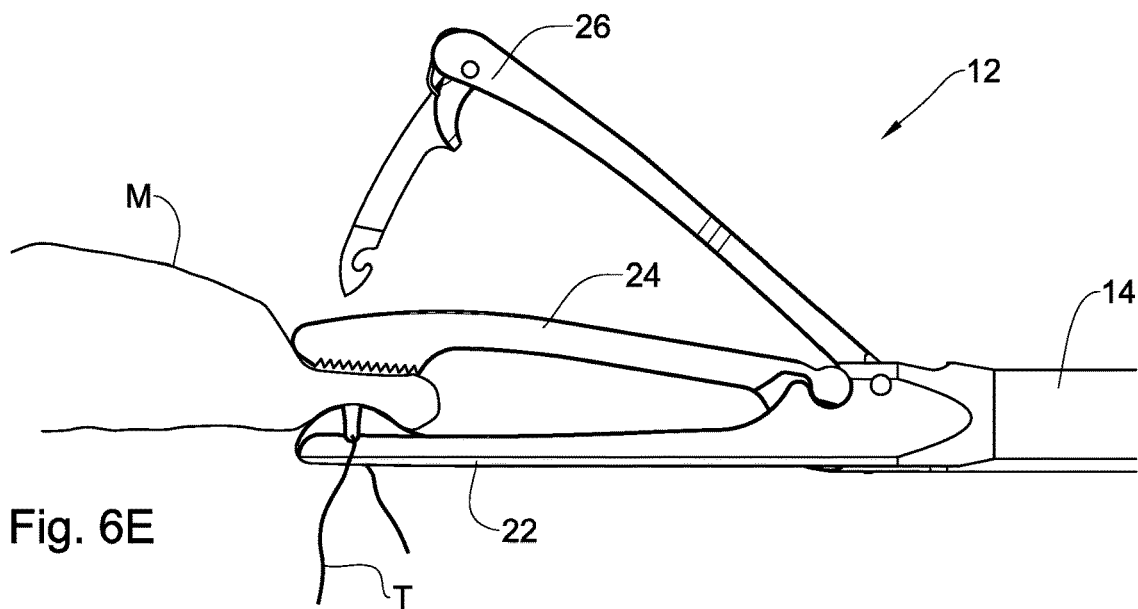

As illustrated in FIG. 6E, the carrying member 26 is brought into its open-carrier position, and the needle 28 is urged into its open-needle position by the biasing member.

Figure 6F:
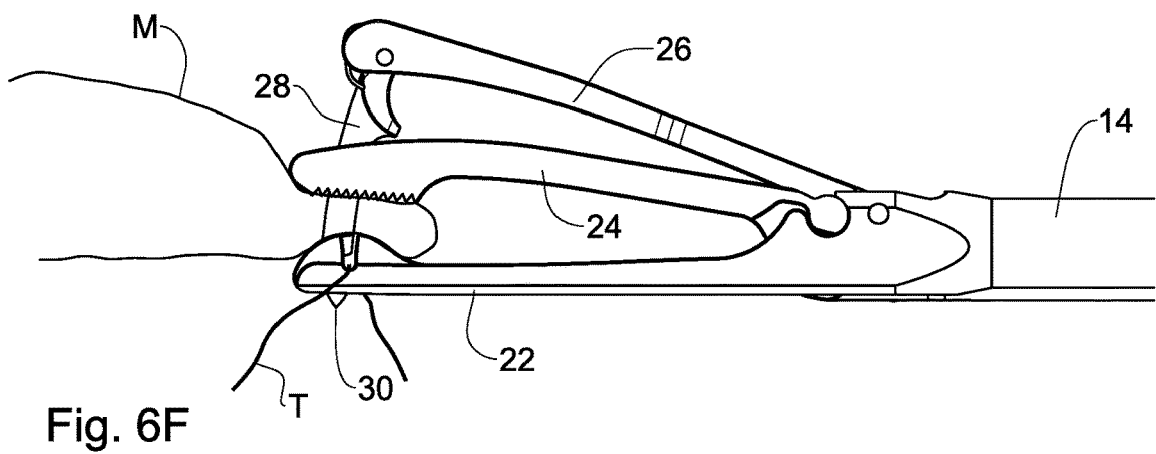

As illustrated in FIG. 6F, the carrying member 26 is brought into its closed-carrier position, while the needle 28 is in its open-needle position. The tip 30 of the needle 28 passes through the upper and lower slots 46, 38 formed in the upper and lower jaw portions 24, 22, thereby impinging upon the tissue M and piercing it.

Figure 6G:
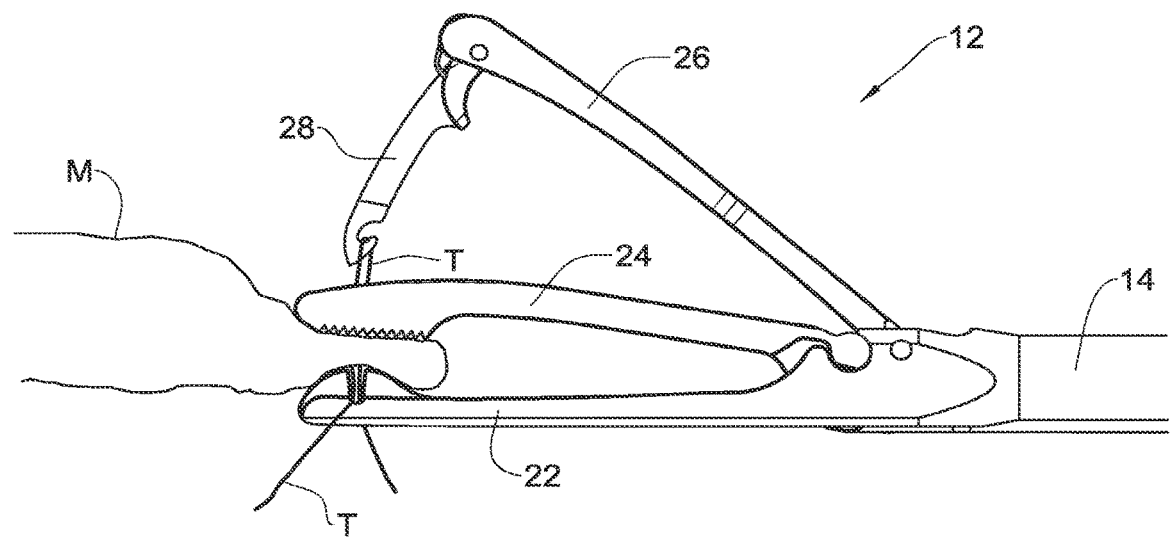

As illustrated in FIG. 6G, the carrying member 26 is returned to its open-carrier position. During this step, the thread T enters the eye 32 of the needle 28 via the opening 36 thereof, and is caught by the hook 34, raising it through the tissue M, thereby performing a suturing operation. The upper jaw portion 24 may be brought into its open-jaw position, and the suturing member 12 withdrawn slightly from the tissue M, i.e., such that it is no longer within the jaw assembly 18.

Figure 6H:
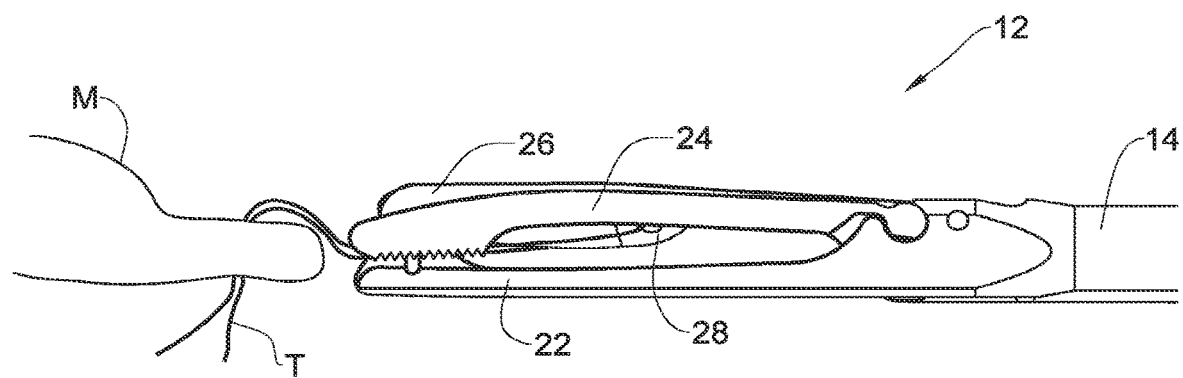

As this stage, a stitch of the suture has been placed in the tissue M. The suturing mechanism 12 may be removed from the patient, along with the thread. According to some examples, the upper jaw portion 24, carrying member 26, and needle 28 are each brought into their respective closed positions, as illustrated in FIG. 6H. As the suturing mechanism 12 is withdrawn (in the direction indicated by arrow W), the thread T may remain within the eye 32 of the needle 28, and/or be retained between the needle and the carrying member 26.

Figure 6I:
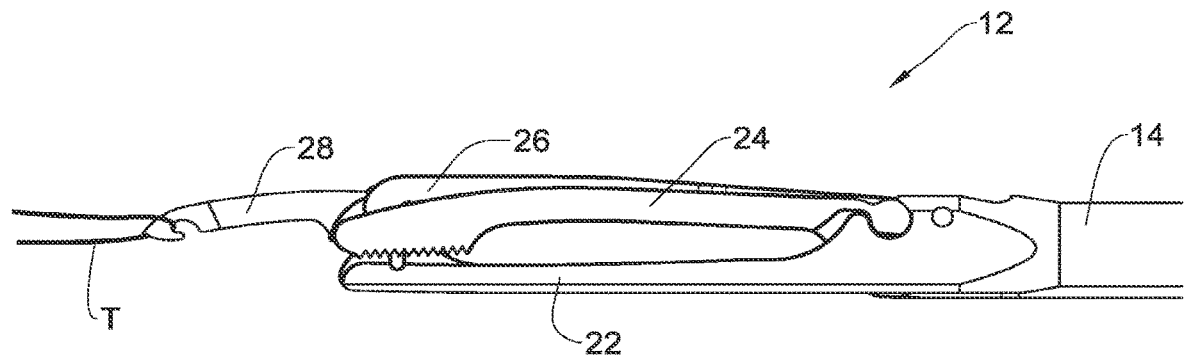

According to other examples, for example as illustrated in FIG. 6I, the needle 28 is configured to be further pivoted to an extended-needle position, in which it is substantially aligned with the carrying member 26 along the longitudinal axis L, with its tip 30 located distally therefrom. Accordingly, the needle 28 may be brought into its extended-needle position from the position illustrated in FIG. 6G and the carrying member 26 brought into its closed-carrier position. The suturing mechanism 12 may then be withdrawn (in the direction indicated by arrow W), with the thread T retained in the eye 32 by the hook 34.

It will be appreciated that the above description of placement of a suture on the tissue of a patient may be employed irrespective of the mechanism used to direct operation of the elements of the suturing mechanism 12. Accordingly, while the handle assembly 16, as described above with reference to and illustrated in FIGS. 3A through 5, may be used to activate the suturing mechanism 12 as described above with reference to and illustrated in FIGS. 2A through 2C, any other suitable mechanism, e.g., a different handle assembly, a computer-controlled mechanism, etc., may be used to carry out the steps described above with reference to and illustrated in FIGS. 6A through 6I, without departing from the scope of the presently disclosed subject matter, mutatis mutandis.

Figure 7A:
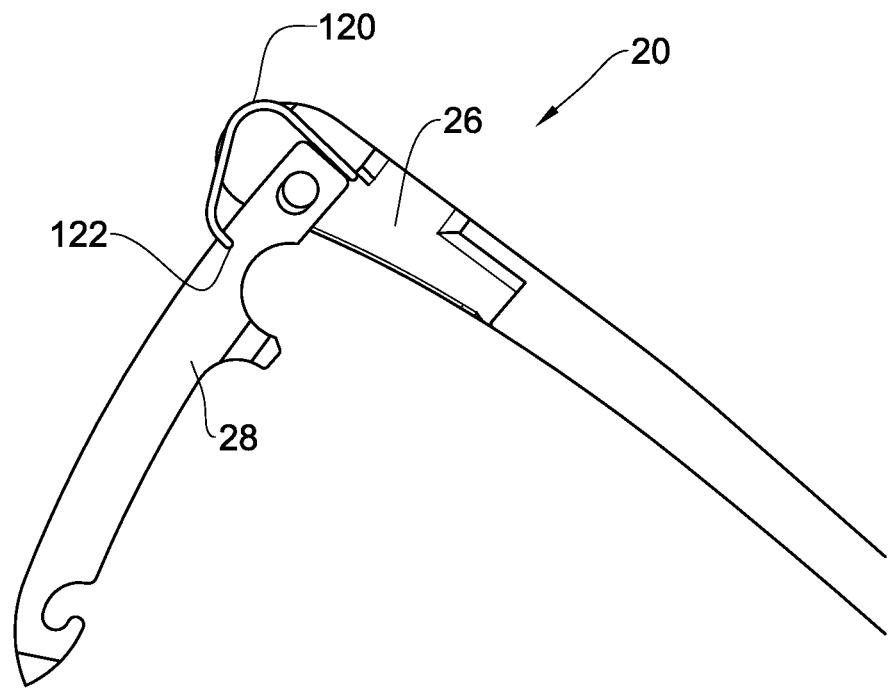
FIGS. 7A and 7B are cross-sectional views, taken along line II-II in FIG. 2A, of a needle mechanism of the suturing mechanism illustrated therein, in respective open-needle and extended-needle positions thereof.
Figure 7B:
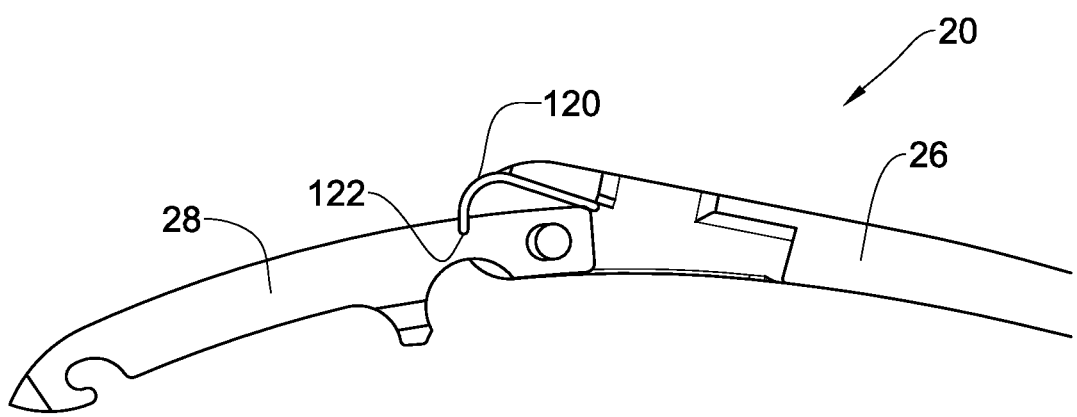

As mentioned above, according to some examples the needle mechanism 20 may be configured to facilitate the needle 28 assuming an extended-needle position. Accordingly, it may be further configured to arrest the needle at its open-needle position, and allow for it be pivoted to its extended-needle position. For example, as illustrated in FIGS. 7A and 7B, the needle mechanism 20 may further comprise a positioning element 120. The needle 28 may be formed with a cavity 122 designed to receive therein one end of the positioning element 120.

The positioning element may be as a flat spring or other suitable biasing element, and is designed in conjunction with the biasing member, i.e., that provided to urge the needle 28 into its open-needle position as mentioned above, to maintain the needle in its open position. I.e., the positioning element 120 is disposed and selected to bear upon the needle 28 in a direction toward its closed-needle position, and to provide an opposing force to that of the biasing member once the needle is in its open-needle position. Accordingly, the needle 28 may autonomously assume its open-needle position under the urging of the biasing member, and be held in place by the opposing force of the positioning element 120.

The needle 28 may be further urged into its extended-needle position by an outside force. Accordingly, in the absence of any outside intervention, the needle 28 assumes its open-needle position when the carrying member 26 is in its open-carrier position, as described above. A user may, e.g., manipulate the suture passer 10 or another implement such that the requisite force is applied on the needle 28 to urge it into its extended-needle position. The positioning element 120 and biasing member may thus constitute a positioning arrangement of the needle mechanism 20, configured to bias the needle 28 to its open-needle position and arrest it there, and to allow it to further assume its extended-needle position.

Figure 8A:
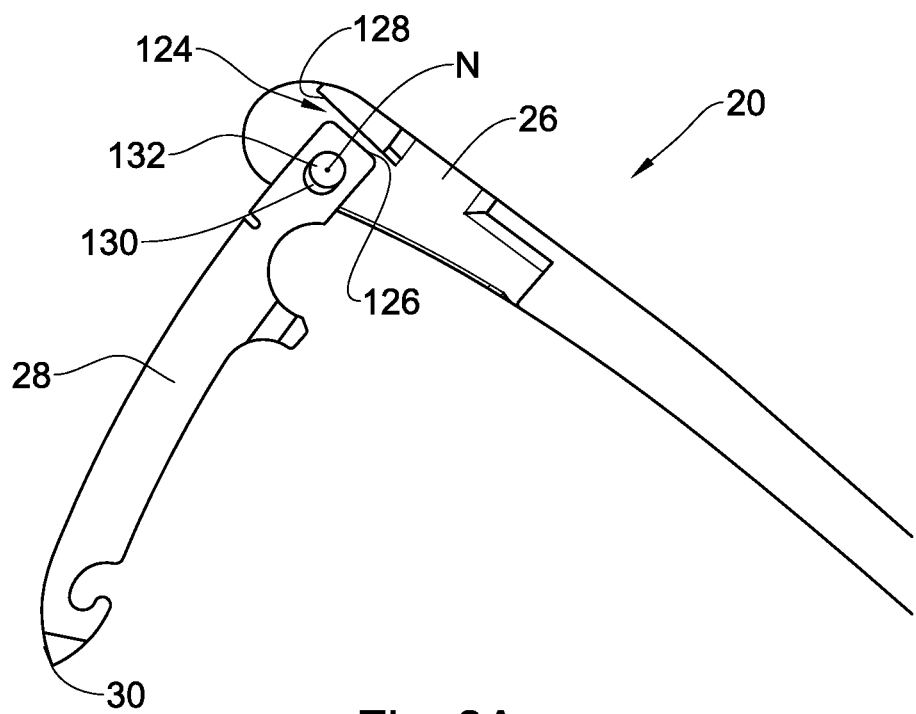
FIGS. 8A and 8B are cross-sectional views, taken along line II-II in FIG. 2A, of the needle mechanism, in respective free and locked positions of a needle thereof.
Figure 8B:
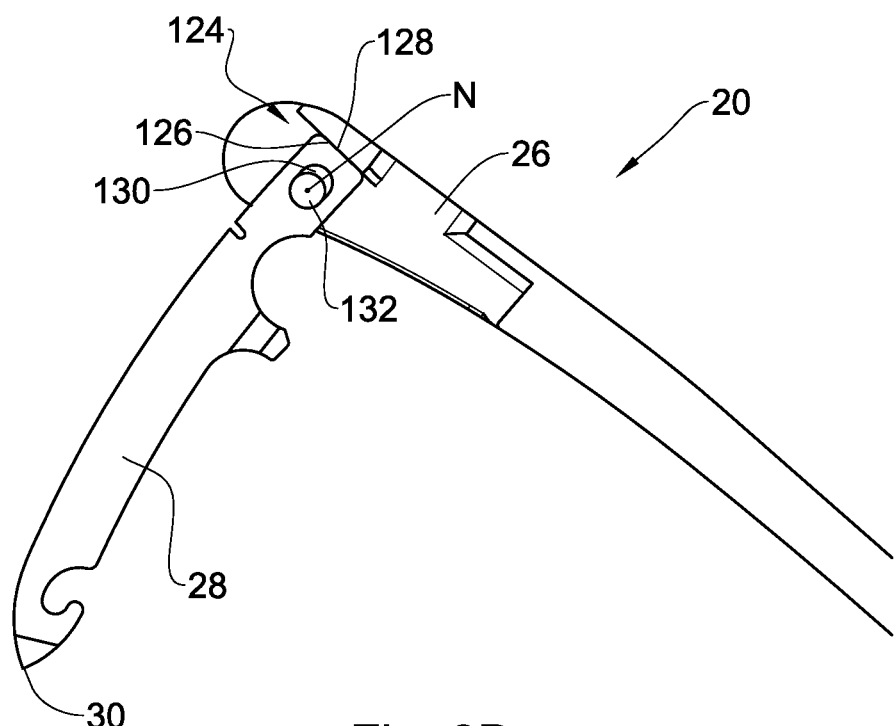

According to some examples, the needle mechanism 20 is configured to permit pivoting of the needle 28 about the needle axis N, and to facilitate selectively securing the needle in its open-needle position. Accordingly, as illustrated in FIGS. 8A and 8B, the needle mechanism may further comprise a locking arrangement, which is generally indicated at 124. The locking arrangement 124 comprises cooperating surfaces 126, 128 of the carrying member 26 and the needle 28, which are formed so as to impede, when engaged with one another, rotation of the needle about the needle axis N. One cooperating surface 126 may constitute a distal end of the needle 28, and the other cooperating surface 128 may constitute a downwardly facing (i.e., facing toward the needle) surface of the carrying member 26. It will be appreciated that the surfaces 126, 128 may be formed so as to so impede the needle 28 when it is in its needle-open position.

In addition, the needle 28 may be configured to be longitudinally (i.e., along its own length) displaced between a free position wherein the cooperating surfaces 126, 128 of the carrying member 26 and the needle 28 are not engaged with one another (as illustrated in FIG. 8A), and a locked position in which they are (as illustrated in FIG. 8B). For example, the needle 28 may comprise a through-going aperture 130 shaped as an obround (i.e., two semicircles connected, at their endpoints, by two tangent lines) for receiving therein a round pin 132. Accordingly, the needle 28 may be displaced proximally into the locked position when a force is applied on the tip 30 thereof, for example when impinging upon the tissue, for example as described above with reference to and illustrated in FIG. 6F.

It will be appreciated that the cooperating surfaces 126, 128 of the carrying member 26 and the needle 28 may be formed in any suitable manner to engage one another. For example, they may each be planar, and face one another when the needle 28 is in its open-needle position. When the needle 28 is distally displaced, the cooperating surfaces 126, 128 bear upon one another (as illustrated in FIG. 8B), thereby impeding pivoting of the needle about the needle axis N. According to other examples (not illustrated), the cooperating surfaces may be formed with corresponding non-planar surfaces, a projection in one and corresponding aperture in the other, etc.

Those skilled in the art to which this invention pertains will readily appreciate that numerous changes, variations, and modifications can be made without departing from the scope of the presently disclosed subject matter, mutatis mutandis.

The invention claimed is:

1. A suture passer defining a longitudinal axis and comprising a jaw assembly configured to be operated to selectively grip an internal tissue of a patient, and a needle mechanism configured to be operated to place a suture on said tissue;

said jaw assembly comprising a stationary first jaw portion and a second jaw portion pivotable about a jaw axis with respect to said first jaw portion between a closed position and an open position, the jaw assembly further comprising a pivoting arrangement configured to facilitate hingedly articulating said first and second jaw portions, the pivoting arrangement being free of a member traversing the jaw assembly parallel to the jaw axis, said jaw assembly being configured to hold a thread for said suture;

said needle mechanism comprising a needle being configured for piercing said tissue and pulling said thread from the jaw assembly, and a carrying member at a first end thereof being pivotable independently of said second jaw portion at least when the second jaw portion is in its closed position with respect to the first jaw portion, said needle being hingedly articulated to a second end of the carrying member between an extended position in which it is disposed distally to said carrying member along a longitudinal axis thereof, an open position in which it is disposed substantially perpendicular to the carrying member, and a closed position in which it lies in registration therewith, the needle mechanism further comprising a biasing member configured to urge the needle from its closed position into its open position, and a positioning element configured to urge the needle from its extended position to its open position, the biasing member and positioning element being configured to maintain the needle in its open position, the needle mechanism further comprising a locking arrangement configured to selectively impede pivoting of said needle when in its open position.

2. The suture passer according to claim 1, further comprising a closing arrangement configured to bring the needle to its closed position when the carrying member is pivoted toward the jaw assembly.

3. The suture passer according to claim 2, wherein the jaw assembly constitutes a portion of said closing arrangement.

4. The suture passer according to claim 1, wherein one of said jaw portions is formed on a surface facing the other jaw portion with a transverse groove for holding the thread.

5. The suture passer according to claim 4, wherein the jaw portion formed with said groove and said needle are disposed on opposite sides of said other jaw portion.

6. The suture passer according to claim 5, wherein a surface of said other jaw portion facing the needle is formed with a seat configured to at least partially receive therein the needle.

7. The suture passer according to claim 4, said groove being formed in said first jaw portion.

8. The suture passer according to claim 1, wherein said first and second jaw portions are each formed with a longitudinal slot configured to allow passage therethrough of the needle in its open position.

9. The suture passer according to claim 1, wherein said pivoting arrangement comprises axially spaced hinge members and corresponding sockets for receiving and permitting rotation therein of said hinge members.

10. The suture passer according to claim 9, wherein said hinge members project from a proximal end of said second jaw portion.

11. The suture passer according to claim 1, further comprising a jaw actuator configured to control pivoting of said second jaw portion, and a carrier actuator configured to control pivoting of said carrying member, independently of said jaw actuator.

12. The suture passer according to claim 11, further comprising a handle mechanism configured to facilitate a user to selectively and independently operate said jaw actuator and said carrier actuator.

13. The suture passer according to claim 12, wherein said handle mechanism is configured such that operation of said carrier actuator to pivot said carrying member to a closed position also operates said jaw actuator to pivot said second jaw portion to its closed position.

14. The suture passer according to claim 1, wherein said positioning element comprises a flat spring.

15. The suture passer according to claim 1, wherein said locking arrangement comprises facing cooperating surfaces of the needle and carrying member, said surfaces being configured to be selectively engaged with each other to impede the pivoting of the needle.

16. The suture passer according to claim 15, wherein said cooperating surfaces are planar.

17. The suture passer according to claim 15, wherein said cooperating surfaces are formed with non-planar surfaces.

18. The suture passer according to claim 15, wherein one of said cooperating surfaces comprises a projection, the other of said cooperating surfaces comprising a corresponding aperture configured to receive it when the needle is in its open position.

19. The suture passer according to claim 15, said needle comprising an oblong aperture receiving a pin therewithin configured to facilitate the needle to be displaced longitudinally when in its open position toward the carrying member, thereby engaging said cooperating surfaces.

* * * * *